US00PP18234P2

(12) United States Plant Patent
Damen

(10) Patent No.: US PP18,234 P2
(45) Date of Patent: Nov. 20, 2007

(54) ***HELENIUM* PLANT NAMED 'RUBY TUESDAY'**

(50) Latin Name: *Helenium hybrida*
Varietal Denomination: Ruby Tuesday

(75) Inventor: Petrus Thomas Damen, Hillegom (NL)

(73) Assignee: Witteman + Co., Hillegom (NL)

( * ) Notice: Subject to any disclaimer, the term of this patent is extended or adjusted under 35 U.S.C. 154(b) by 0 days.

(21) Appl. No.: 11/450,828

(22) Filed: Jun. 9, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Helenium* plant named 'Ruby Tuesday', characterized by its upright, somewhat outwardly spreading and uniform plant habit; moderately vigorous growth habit; freely flowering habit; inflorescences with dark red-colored ray florets; and strong peduncles that hold the inflorescences above the foliar plane.

1 Drawing Sheet

Botanical designation: *Helenium hybrida.*
Cultivar denomination: 'Ruby Tuesday'.

BACKGROUND OF THE INVENTION

The present invention relates to a new and distinct cultivar of *Helenium* plant, botanically known as *Helenium hybrida,* and hereinafter referred to by the name 'Ruby Tuesday'.

The new *Helenium* is a product of a planned breeding program conducted by the Inventor in Hillegom, The Netherlands. The objective of the program is to create and develop new *Helenium* cultivars with double inflorescence form, sterile flowers and a long flowering period.

The new *Helenium* originated from a cross-pollination by the Inventor in 1998 of two unnamed selections of *Helenium hybrida,* not patented. The new *Helenium* was discovered and selected by the Inventor as a single flowering plant within the progeny of the stated cross-pollination in a controlled environment in Hillegom, The Netherlands in 1999.

Asexual reproduction of the new *Helenium* by terminal cuttings in a controlled environment in Hillegom, The Netherlands since 1999, has shown that the unique features of this new *Helenium* are stable and reproduced true to type in successive generations.

SUMMARY OF THE INVENTION

The cultivar Ruby Tuesday has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Ruby Tuesday'. These characteristics in combination distinguish 'Ruby Tuesday' as a new and distinct cultivar of *Helenium:*

1. Upright, somewhat outwardly spreading and uniform plant habit.
2. Moderately vigorous growth habit.

3. Freely flowering habit.
4. Inflorescences with dark red-colored ray florets.
5. Strong peduncles that hold the inflorescences above the foliar plane.

In side-by-side comparisons conducted in Hillegom, The Netherlands, plants of the new *Helenium* differed from plants of the parent selections primarily in plant form as plants of the new *Helenium* were more compact than plants of the parent selections.

Plants of the new *Helenium* can be compared to plants of the *Helenium* cultivar Rubinzwerg, not patented. In side-by-side comparisons conducted in Hillegom, The Netherlands, plants of the new *Helenium* differed from plants of the cultivar Rubinzwerg in the following characteristics:

1. Plants of the new *Helenium* were more compact than plants of the cultivar Rubinzwerg.
2. Plants of the new *Helenium* were more freely flowering than plants of the cultivar Rubinzwerg.
3. Plants of the new *Helenium* had smaller inflorescences than plants of the cultivar Rubinzwerg.
4. Ray florets of plants of the new *Helenium* were darker red in color than ray florets of plants of the cultivar Rubinzwerg.

BRIEF DESCRIPTION OF THE PHOTOGRAPH

The accompanying photograph illustrates the overall appearance of the new *Helenium.* This photograph show the colors as true as it is reasonably possible to obtain in colored reproductions of this type. Colors in the photograph may differ slightly from the color values cited in the detailed botanical description which accurately describe the colors of the new *Helenium.* The photograph comprises a side perspective view of a typical flowering plant of 'Ruby Tuesday' grown in a container.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in Hillegom, The Netherlands during the summer in an outdoor nursery and under conditions and practices which approximate those generally used in commercial *Helenium* production. During the production of the plants, day temperatures ranged from 14° C. to 31° C. and night temperatures ranged from 4° C. to 16° C. Measurements and numerical values represent averages for typical flowering plants. Plants were about one year old when the photographs and description were taken.

Botanical classification: *Helenium hybrida* cultivar Ruby Tuesday.

Parentage:

*Female, or seed, parent.*—Unnamed selection of *Helenium hybrida,* not patented.

*Male, or pollen, parent.*—Unnamed selection of *Helenium hybrida,* not patented.

Propagation:

*Type.*—Terminal vegetative cuttings.

*Time to initiate roots.*—About two weeks.

*Time to produce a rooted cutting.*—About three to four weeks.

*Root description.*—Fine.

*Rooting habit.*—Freely branching; dense.

Plant description:

*Appearance and growth habit.*—Perennial herbaceous container and cut flower plant. Upright and somewhat outwardly spreading plant habit; inverted triangle. Freely basal branching with about six primary branches. Moderately vigorous growth habit.

*Plant height.*—About 61 cm.

*Plant width or area of spread.*—About 39 cm.

*Lateral branch description.*—Appearance: Mostly rounded with four vertical "wings"; wings about 2 mm in depth and dull in appearance. Length: About 52 cm. Diameter: About 6 mm. Internode length: About 2.6 cm. Strength: Strong. Texture: Smooth, glabrous. Color: 144B; wings, 143A.

Foliage description:

*Arrangement.*—Alternate; simple; sessile.

*Length.*—About 9.3 cm.

*Width.*—About 2.3 cm.

*Shape.*—Narrowly elliptic to narrowly ovate.

*Apex.*—Acute.

*Base.*—Cuneate; decurrent.

*Margin.*—Dentate.

*Venation pattern.*—Pinnate.

*Texture, upper and lower surfaces.*—Smooth, glabrous.

*Color.*—Developing foliage, upper surface: Between 137A and 143A. Developing foliage, lower surface: 138A. Fully expanded foliage, upper surface: 137A; venation, 144A. Fully expanded foliage, lower surface: 137B to 137C; venation, 144A.

Inflorescence description:

*Appearance/arrangement.*—Single terminal and axillary inflorescences held above the foliage on strong erect peduncles. Composite inflorescence form, radially symmetrical; flabellate-shaped ray florets; disc florets massed at the center; ray and disc florets develop acropetally on a capitulum. Inflorescences face mostly upright.

*Flowering response.*—Plants flower continuous and freely from midsummer to late summer in The Netherlands. Inflorescences persistent.

*Postproduction longevity.*—Inflorescences maintain good color and substance for about three weeks on the plant and about two weeks as cut flowers.

*Quantity of inflorescences.*—Freely flowering habit; about 180 inflorescences per plant develop during the flowering season.

*Fragrance.*—None detected.

*Inflorescence bud.*—Length: About 9 mm. Diameter: About 1 cm. Shape: Flattened globular. Color: N144A.

*Inflorescence size.*—Diameter: About 3.8 cm. Depth (height): About 1.8 cm. Disc diameter: About 1.6 cm. Receptacle height: About 5 mm. Receptacle diameter: About 3 mm.

*Ray florets.*—Length: About 1.8 cm. Width: About 9 mm. Shape: Narrowly flabellate. Apex: Tri-lobed. Base: Attenuate. Margin: Entire. Texture, upper and lower surfaces: Mostly smooth; towards the base, pubescent. Orientation: Initially upright then perpendicular to the peduncle. Number of ray florets per inflorescence: About 16 in a single whorl. Color: When opening, upper surface: 187B. When opening, lower surface: 187A to 187B. Fully opened, upper surface: Between 53A and 187B; color becoming closer to 185A with development. Fully opened, lower surface: 183B.

*Disc florets.*—Shape: Tubular, elongated. Apex: Five-pointed; acute. Length: About 4 mm. Width, apex: About 1 mm. Width, base: About 0.8 mm. Number of disc florets per inflorescence: Numerous, about 600. Color immature: 13A to 13B; towards the apex, N186C. Color, mature: Apex: Darker than N186C. Mid-section: 13A to 13B. Base: 145D.

*Phyllaries.*—Length: About 1.2 mm. Diameter: About 1.5 mm. Shape: Linear. Apex: Acute. Base: Cuneate. Margin: Entire. Texture, upper and lower surfaces: Smooth, glabrous. Number per inflorescence: About 16 in a single whorl. Color, upper surface: 143B. Color, lower surface: 143A.

*Peduncles.*—Length, terminal peduncle: About 5.6 cm. Length, fourth peduncle: About 17.6 cm. Length, seventh peduncle: About 21.5 cm. Diameter: About 2 mm. Angle: Mostly erect to about 10° from vertical. Strength: Moderately strong. Texture: Smooth, glabrous. Color: 143A.

*Reproductive organs.*—Androecium: Present on disc florets only. Stamen number: Five per floret. Anther shape: Linear. Anther length: About 2 mm. Anther color: 162C. Pollen amount: None observed. Gynoecium: Present on both ray and disc florets. Pistil number: One per floret. Pistil length: About 3 mm. Stigma shape: Rounded. Stigma color: 12A. Style length: About 2 mm. Style color: 150D. Ovary color: 150C.

*Fruit/seed.*—Fruit and seed development have not been observed.

Disease/pest resistance: Resistance to pathogens and pests common to *Helenium* has not been observed on plants grown under outdoor conditions.

Garden performance: Plants of the new *Helenium* have been observed to have good garden performance and to tolerate rain, wind and temperatures from about 0° to about 35° C.

It is claimed:

1. A new and distinct *Helenium* plant named 'Ruby Tuesday' as illustrated and described.

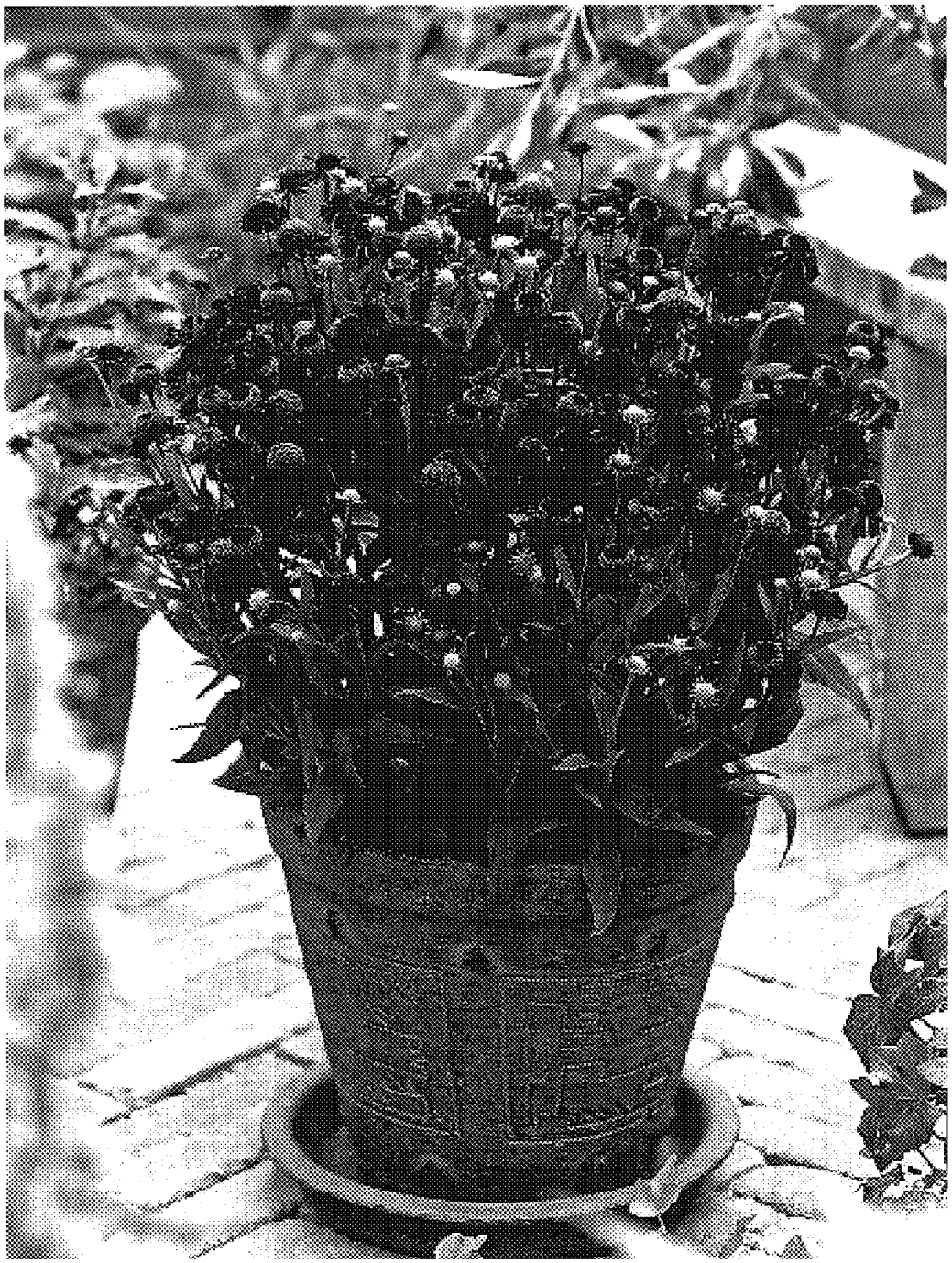

* * * * *